(12) United States Patent
Nickerson

(10) Patent No.: US 7,249,523 B2
(45) Date of Patent: Jul. 31, 2007

(54) APPARATUS AND METHOD FOR MEASURING MECHANICAL PROPERTIES

(75) Inventor: Charles Nickerson, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 110 days.

(21) Appl. No.: 11/123,452

(22) Filed: May 6, 2005

(65) Prior Publication Data
US 2005/0247137 A1 Nov. 10, 2005

Related U.S. Application Data

(60) Provisional application No. 60/568,834, filed on May 6, 2004.

(51) Int. Cl.
*G01N 3/24* (2006.01)
(52) U.S. Cl. .................. 73/846; 73/856; 73/859; 73/860
(58) Field of Classification Search ............ 73/846
See application file for complete search history.

(56) References Cited

U.S. PATENT DOCUMENTS

| | | | | |
|---|---|---|---|---|
| 4,343,190 A | * | 8/1982 | Danko et al. ............ | 73/846 |
| 5,079,956 A | * | 1/1992 | Burhin et al. ............ | 73/846 |
| 5,349,847 A | * | 9/1994 | Lee et al. ................ | 73/54.28 |
| 5,357,783 A | * | 10/1994 | Eschbach .................. | 73/54.33 |
| 5,610,325 A | * | 3/1997 | Rajagopal et al. ........ | 73/54.39 |
| 6,815,015 B2 | * | 11/2004 | Young et al. ............. | 427/596 |
| 6,962,086 B2 | * | 11/2005 | Prescott et al. .......... | 73/846 |
| 6,978,662 B2 | * | 12/2005 | Platzek et al. ........... | 73/54.42 |
| 7,049,147 B2 | * | 5/2006 | Sentmanat ................ | 436/55 |
| 7,054,766 B2 | * | 5/2006 | O'Brien .................. | 702/50 |

* cited by examiner

*Primary Examiner*—Edward Lefkowitz
*Assistant Examiner*—Freddie Kirkland, III
(74) *Attorney, Agent, or Firm*—Myers Dawes Andras & Sherman LLP

(57) ABSTRACT

A rheological measurement can be made comprising the steps of disposing a sample to be measured between two opposing surfaces of a fixture; coupling two opposing surfaces of the sample with a corresponding adjacent one of the two opposing surfaces of the fixture to create a secondary sample boundary within the sample; and measuring a rheological parameter of the sample. The two opposing surfaces of the sample are coupled with a corresponding adjacent one of the two opposing surfaces of the fixture by penetrating at least one of the opposing surfaces of the sample with a plurality of protrusions disposed on the corresponding surface of the fixture.

17 Claims, 5 Drawing Sheets

APPARATUS AND METHOD FOR MEASURING MECHANICAL PROPERTIES

RELATED APPLICATIONS

The present application is related to U.S. Provisional Patent Application, Ser. No. 60/568,834, filed on May 6, 2004, which is incorporated herein by reference and to which priority is claimed pursuant to 35 USC 119.

BACKGROUND OF THE INVENTION

1. Field of the Invention

The invention relates to apparatus and methods of testing or measuring the bulk mechanical properties of most liquid, gel, and solid materials.

2. Description of the Prior Art

Probing the bulk mechanical properties of most liquid, gel, and solid materials requires applying some form of deformation, often a shear pulse, and measuring the response of the sample. Devices designed to measure such properties include viscometers, rheometers, texture analyzers, and materials testers. To function properly, the tool surfaces of these devices must remain firmly adhered to the test sample; wall slip at either the deformation-side or detection-side interface interferes with testing. But many important materials, including biological tissues, foods, swollen gels, and other dispersed systems, form depletion layers at the interface. Depletion layers and other mechanisms of wall slip can present a significant barrier to investigating affected materials.

Previous attempts to overcome wall slip can be divided into two broad categories, surface modifications to existing geometries and novel geometries. One important rheometric tool to which surface modifications have been made is the parallel plate tool geometry. In the parallel plate tool geometry, the sample is placed between two parallel, smooth discs. As one disc displaces the sample, the other disc measures the magnitude and phase of the resulting stress. The no-slip boundary condition mentioned above is a crucial assumption in all shear rheometry measurements. Surface modifications have included physically roughening, chemically modifying, and scoring tool surfaces with grooves or cross-hatch patterns. But these modifications are not enough to overcome slip in swollen gels and other samples in which a significant lubricating layer develops. Often pressure (normal force) must be applied to maintain good contact. Application of normal force interferes with accurate measurements because it changes the rheological properties of the sample. It can also destroy delicate network structures. Also, irregular surface features may induce complex flow patterns and ill-defined deformation at the tool surface.

More exotic geometries have also been invented for specific applications, such as the vane and helix geometries. Three issues that hinder wide-spread embrace of these tools follow: 1) they often require large sample volumes. 2) determining true rheological properties such as viscosity, modulus etc. is experimentally difficult if possible at all, and 3) most are not suitable for use with delicate samples such as swollen gels and soft biological samples.

What is needed is some type of apparatus and method of measuring the mechanical properties of materials that overcomes each of the foregoing limitations of the prior art.

BRIEF SUMMARY OF THE INVENTION

The "cleat" test geometry of the illustrated embodiment overcomes many of the limitations mentioned above. The geometry of the illustrated embodiment is a modified parallel plate tool with a large number of uniform protrusions or "cleats" extending from the faces of the plates. This unique geometry for slip prevention in shear combines the advantages of small sample size, a gentle loading procedure, negligible normal force, and direct measurement of shear modulus. It is also far easier to clean and more robust against physical damage, solvents, and high temperatures than sandpaper or glass frits.

An advantageous feature of the tool is the uniformity of cleat length ($L_c$, distance from plate face to cleat tip). The significance of uniformity is that the cleat tips create a well-defined plane within the sample that is parallel to the plate face. Motion of fluid between the cleats is restricted and decays to zero a short distance ($\delta$) into the tool. The depth at which fluid motion is stopped establishes the effective sample gap boundary. The position of this effective sample boundary is independent of the fluid measured in all materials examined and can be estimated from the geometric parameters of the cleats and verified empirically, as will be discussed below. Using the effective sample gap ($gap_{eff} = gap_{meas} + 2\delta$) rather than the measured sample gap ($gap_{meas}$) is the only procedural difference between cleat geometry and smooth plate experiments.

The effective sample gap is estimated by treating the array of cleats as a porous material and determining the flow field within it. From measurements of the in-plane, pressure-driven flow through an array of cleats analogous to the tool, the permeability of the cleat geometry was calculated using Darcy's law ($k = 8.7 \times 10^{-10} m^2$). Flow of a Newtonian fluid over a porous medium has been analyzed extensively in the prior art where it was shown that the resulting motion of fluid within the porous medium is attenuated over a short distance ($\delta$) that is related to the permeability k ($\delta \propto k^{1/2}$) and is independent of the viscosity of the fluid. In highly porous media, such as the cleat geometry it has been predicted that an exponential velocity decay profile such that the fluid velocity in the porous region will be reduced to <1% of the boundary velocity when $\delta \sim 5 \cdot k^{1/2}$ (~150 μm in the present cleat geometry). Since the attenuation depth is insensitive to fluid properties, the value of $\delta$ for Newtonian fluids provides a good approximation for viscoelastic materials as well.

The disclosure demonstrates the accuracy and utility of the cleat geometry. For this purpose, results obtained with the cleated tools are compared with those obtained using smooth and roughened parallel plate geometries. First, for fluids that do not exhibit slip, the results confirm that quantitative measurements can be obtained using a single value of the gap correction $\delta$. The empirical value for $\delta$ based on these fluids is compared with $k^{1/2}$ to evaluate the applicability of the porous medium analogy. Next we show that the tool performs well when applied to two fluids that exhibit moderate slip, and we validate the results independently using roughened plates. Finally, the power of the new geometry is illustrated by obtaining modulus measurements for porcine vitreous humor, a biological tissue that cannot be handled successfully with prior tools.

The illustrated embodiment of the invention is a method of making a rheological measurement comprising the steps of disposing a sample to be measured between two opposing surfaces of a fixture; coupling two opposing surfaces of the sample with a corresponding adjacent one of the two opposing surfaces of the fixture to create a secondary sample boundary within the sample; and measuring a rheological parameter of the sample.

The step of coupling two opposing surfaces of the sample with a corresponding adjacent one of the two opposing surfaces of the fixture comprises penetrating at least one of the opposing surfaces of the sample with a plurality of protrusions disposed on the corresponding surface of the fixture.

The sample has a bulk bounded by its surfaces and the step of penetrating at least one of the opposing surfaces of the sample with protrusions disposed on the corresponding surface of the fixture comprises disposing a plurality of protrusions into the bulk of the sample.

The plurality of protrusions have distal ends and where the step of coupling two opposing surfaces of the sample with a corresponding adjacent one of the two opposing surfaces of the fixture to create a secondary sample boundary within the sample comprises creating the secondary sample boundary on a plane in the sample defined by or relative to the body shaft length of the plurality of protrusions.

The step of creating the secondary sample boundary at a distal plane in the sample defined by the distal ends of the plurality of protrusions comprises creating the secondary sample boundary in the sample at the distal ends of the plurality of protrusions, or creating the secondary sample boundary in the sample in the proximity to the body shafts of the plurality of protrusions.

The step of coupling two opposing surfaces of the sample with a corresponding adjacent one of the two opposing surfaces of the fixture to create a secondary sample boundary within the sample comprises trapping a portion of the sample adjacent to the surface of the sample. In one embodiment the step of trapping a portion of the sample adjacent to the surface of the sample comprises trapping the portion of the sample in a plurality of protrusions. In another embodiment the step of trapping the portion of the sample in a plurality of protrusions comprises incorporating the secondary sample boundary into the trapped portion. In still a further embodiment the step of coupling two opposing surfaces of the sample with a corresponding adjacent one of the two opposing surfaces of the fixture to create a secondary sample boundary within the sample comprises penetrating a depletion layer on the sample.

The step of measuring a Theological parameter of the sample comprises measuring the rheological parameter between a contiguous sample-to-sample interface created by the secondary sample boundary.

The invention also includes a fixture with which the above described methodologies may be practiced. Many different embodiments of the fixture may be so employed.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The invention can be characterized as directed to a cleat tool geometry. The illustrated embodiment provides an example of how the limitations of the prior art have been surmounted. In the illustrated embodiment, what is described is a measurement of the shear moduli of the intact vitreous humor of the human eye using what is defined in this specification as cleat tool geometry.

Figure 1:
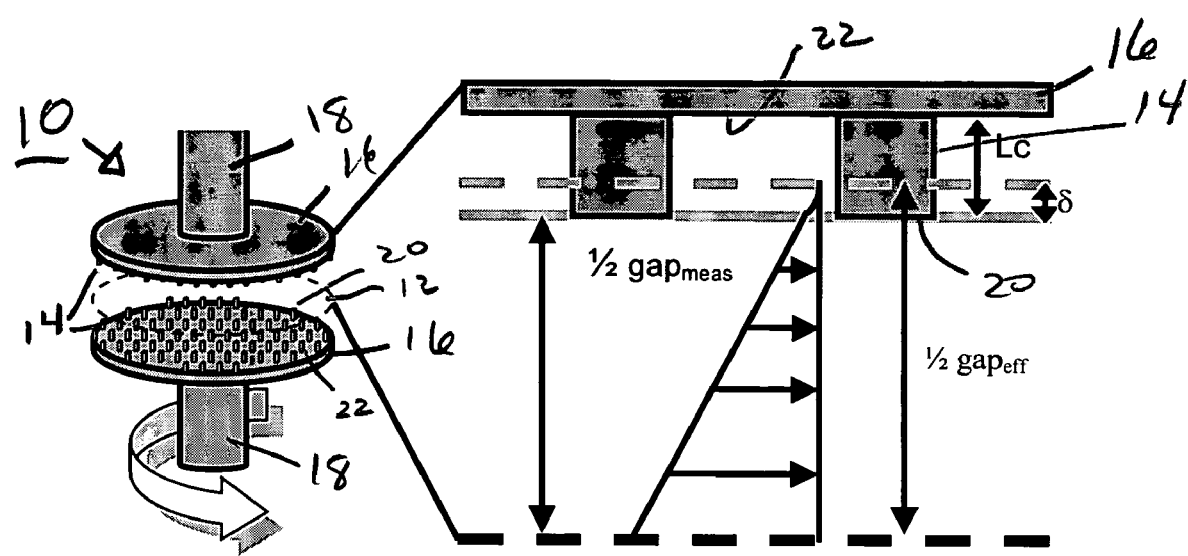
FIG. 1 is a diagrammatic representation of two cleated fixtures placed opposite each other. Sample motion penetrates only a short distance δ into the cleat array. The actual cleat density is high, approximately $100/cm^2$. The portion of the diagram on the right of the drawing is an enlarged cross-sectional view of the cleat and sample geometry taken through a radius of the disc from the disc surface to the midline of the sample.

The illustrated cleat geometry is based upon the well-defined physics of the parallel plate geometry for shear measurements; but rather than smooth discs, the fixture 10 which contacts the sample 12 has at least one cleated surface 22. FIG. 1 is a diagrammatic perspective depiction of the illustrated embodiment. Fixture 10 is comprised of two opposing discs 16, whose opposing inner surfaces 22 are each provided with a plurality of protrusions or cleats 14. The term "protrusion" or "cleat" will be used interchangeably through the specification and are to be understood in the broadest sense as illustrated by the disclosure. Discs 16 are coupled to stems 18, which in turn are coupled to conventional rheological elements (not shown) for applying a measured amount of rotational shear and measuring the resulting relative rotational stress exerted between discs 16 with sample 12 therebetween, or vice versa. Protrusions 14 are arranged in a regular array, but may be disposed on surfaces 22 in any pattern desired, including in a random distribution. In the illustrated embodiment, each protrusion 14 is in the form of a right square post, but any shape may be employed and the free or end of each protrusion 14 distal from surface 22 provided with any desired shape, termination, coating or treatment.

The densely-packed protrusions 14 defined on fixture 10 penetrate any lubricating boundary or depletion layers that may develop at the surface 22 of disc 16 and extend into the bulk of the sample 12. Thus, a portion of the sample 12 is immobilized within the area between the protrusions 14 of each disc 16. It is highly desired that all or substantially all of the protrusions 14 extend the same length from the surface 22 of the disc 16 so that the distal tips 20 of the protrusions 14 form what is defined in this specification as a "secondary sample boundary". The densely-packed protrusions 14 prevent flow between them for materials exhibiting at least some solid-like character or storage modulus as well as simple Newtonian fluids with a wide range of viscosities. Thus, slip layers that form at the disc surface 22 do not prohibit the fixture 10 from griping the sample 12 and no normal force applied to sample 12 is required.

In the preferred embodiment of the invention, for an appropriate longitudinal length of protrusions 14, surface area of disc 16, and density of protrusions 14, the sample 12 trapped between protrusions 14 moves with them. Thus, at the secondary boundary, slip is absent because the interface between fixture 10 and sample 12 is effectively a contiguous sample-to-sample junction. In effect the secondary sample boundary becomes the effective disc-to-sample boundary for rheological purposes. Because the no-slip boundary condition is met at the secondary boundary, a proper rheometric deformation is imposed and the distance between no-slip boundaries is used in calculating rheological properties.

By direct analogy to the parallel plate geometry, we can measure true rheological properties using the space between the secondary sample boundaries of opposing discs 16 as the effective thickness of the sample gap. Using a series of viscoelastic materials possessing a large range of shear moduli, we have shown that results obtained with the cleat geometry compare favorably with results obtained using parallel plates.

In the illustrated embodiment four different tools were used to measure shear moduli and viscosities of a variety of materials from low viscosity Newtonian oils to slippery biological tissues. The primary reference tool was a smooth 25 mm titanium parallel plate test geometry 10 as shown in FIG. 1 and described above. A rough tool was made by attaching fine emery cloth to the surface of a 25 mm aluminum parallel plate geometry. The two cleated tools 10 were also 25 mm in diameter. Cleats were machined into an aluminum disk leaving protrusions 14 with a square cross section 0.45 mm×0.45 mm, evenly spaced 1.35 mm apart (center to center). Two cleat lengths ($L_c$) were used: 0.6 mm and 1.3 mm. In addition, a vaned fixture and porous plates were used when roughened plates failed (on vitreous humor), but they were also unsatisfactory. The tools 10 were all mounted on an ARES-RFS fluids rheometer (T.A. Instruments, Inc., USA) with sample gaps ranging from 2.25 mm to 0.3 mm. The in-plane permeability of the cleated tools 10 was measured by Porous Materials, Inc. (Ithaca, N.Y.).

Four of the test fluids were selected specifically because they are not prone to slip: a series of three silicone oils, ($\eta$=10, 1.0, and 0.1 Pa·s respectively) and GE Silicones SE-30 poly-dimethyl siloxane (PDMS) putty (Waterford, N.Y.). The 10 Pa·s fluid was methyl silicone oil purchased from Nye Lubricants, Inc. (New Bedford, Mass.); the 1.0 and 0.1 Pa·s oils were silicone viscosity standards from Brookfield Engineering Laboratories, Inc. (Middleboro, Mass.). In experiments on these fluids only the upper disc 16 was cleated, the surface of the lower disc 16 was smooth. Using a smooth lower disc 16 allowed us to validate the cleats at large sample gaps with low viscosity fluids. Each fluid was tested at least three times per sample gap at 22° C. at multiple shear rates (1-80 $s^{-1}$) or frequencies ($10^{-1}$-$10^2$ rad/s), the PDMS putty was tested in the linear viscoelastic regime ($\gamma$=0.2%).

To demonstrate the utility of the cleated geometry for samples that slip, two food products and one biological tissue were characterized using smooth, rough, and cleated tools 10 (both upper and lower fixtures). The foods used were Kroger brand "Real Mayonnaise" (Kroger Co., Cincinnati, Ohio), an oil in water emulsion, and Winn-Dixie brand "Creamy Peanut Butter" (Winn-Dixie Stores, Inc., Jacksonville, Fla.), a suspension, both of which exhibit slip on smooth tools 10. Samples were tested at least three times at 5° C. at multiple shear rates ($10^{-2}$-10 $s^{-1}$). The biological tissue was fresh porcine vitreous humor acquired through Sierra for Medical Science (Santa Fe Springs, Calif.), which is an example of a delicate hydrogel that exhibits slip even on rough tools 10. Eyes from 3-6 month old swine were enucleated immediately after the animals were sacrificed and shipped at ~5° C. in physiological saline. Fresh eyes were gently dissected between 24 and 36 hours post mortem (no vitreous degradation is seen within ~48 hours) to remove the vitreous with minimal disruption. From the intact vitreous, a disc-like section was cut with the axis of the disc coinciding with the anterior-to-posterior axis of the eye (typically 1.5-2.5 g). The samples were approximately 25 mm in diameter; to mitigate the effects of drying a vapor trap was used. All measurements were made at 20° C. with zero normal force on the samples ($\gamma$=3%, $\omega$=10 rad/s).

Figure 2A:
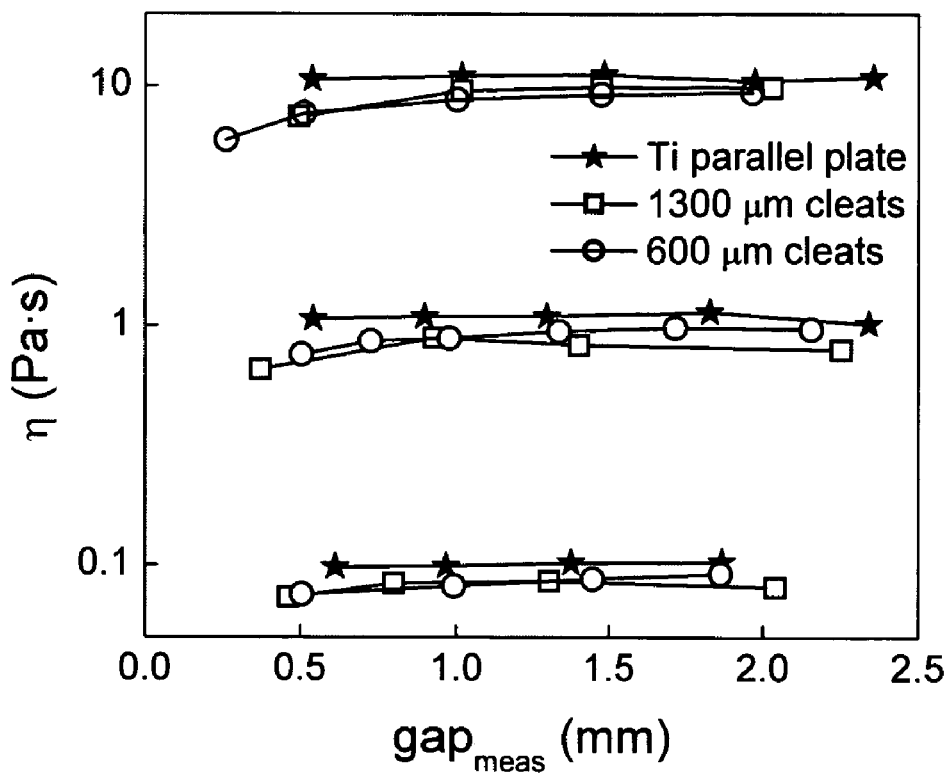
FIGS. 2a and 2b are graphs of the measured viscosity verses gap size in FIG. 2a and the ratio of measured viscosity to true viscosity as measured by the smooth plates verses gap size in FIG. 2b.

Consider the results for the Newtonian Oils. The viscosities of three silicone oils were measured with the smooth parallel plate geometry and with one of the parallel plates replaced by a cleated tool 10. Two different cleat lengths (600 μm and 1300 μm) were compared. At least four different sample gap values were tested for each tool configuration. For smooth tools, the measured viscosity is independent of gap as shown in the graph of FIG. 2a. The viscosity obtained with cleated tools is insensitive to gap thickness when $gap_{meas} \geq 1$ mm, indicating $\delta \ll 1$ mm. The results are also insensitive to cleat length (cf. $L_c$=0.6 and 1.3 mm), which indicates $\delta$<600 μm, in accord with the porous-medium prediction of $\delta$~150 μm.

Figure 2B:
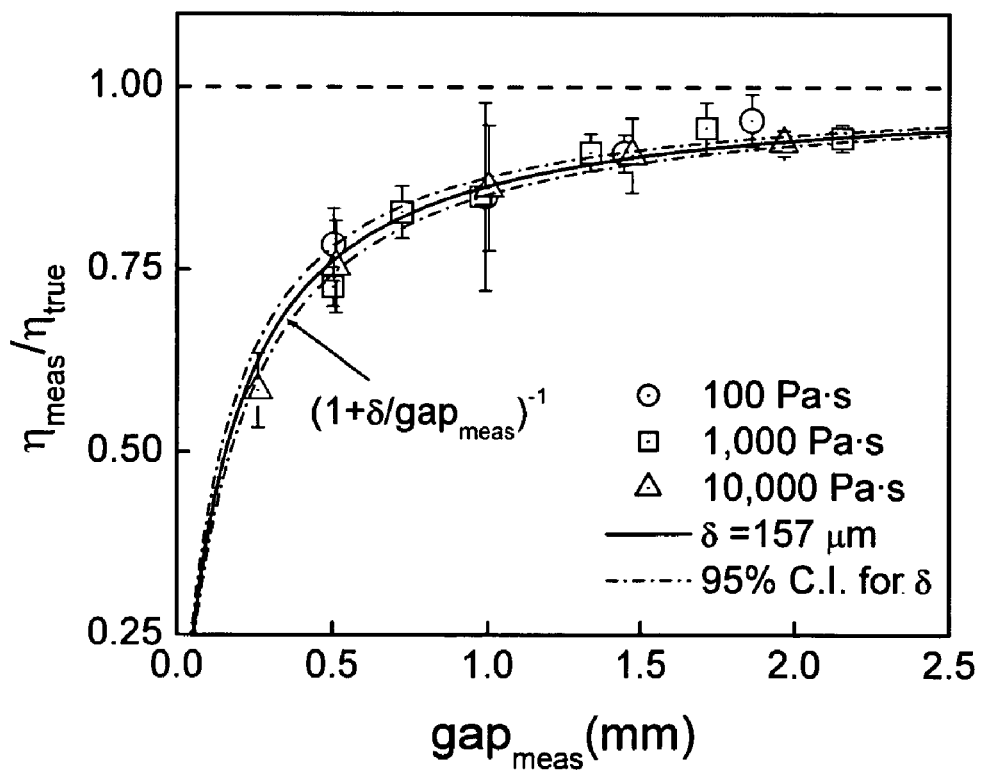

FIGS. 2a and 2b illustrate that the cleat geometry of the invention yields uncorrected viscosities that are close to but systematically lower than values obtained using a titanium parallel plate geometry (shear rate=10 $s^{-1}$). Measured viscosity is independent of cleat length, $L_c$, for all of three silicone oils. Viscosity measured using the cleat geometry divided by true viscosity, measured by the smooth plates. The solid curve shows the predicted gap dependence $(1+\delta/gap^{meas})^{-1}$ with a value of $\delta$=157 μm. Dashed curves bound the 95% confidence interval (141 μm<$\delta$<173 μm).

Experimentally-determined correction values also compare favorably with predictions. Based on the porous-medium analogy, the gap-dependent disparity between viscosity measurements from smooth ($\eta_{true}$) and cleated tools ($\eta_{meas}$) is predicted to be $\eta_{meas}/\eta_{true}=gap_{meas}/(gap_{meas}+\delta)$. Note that $\delta$ would be replaced by 2$\delta$ if both faces were cleated rather than just the upper tool. This expression accords well with the experimental results as a function of gap as shown in the graph of FIG. 2b. A single value of $\delta$ holds for all three Newtonian oils. Non-linear least squares fitting of $\eta_{meas}/\eta_{true}$ to $(1+\delta/gap_{meas})^{-1}$ yields an empirical value of $\delta=157$ μm (95% CI=141-173 μm), in remarkably good agreement with the predicted value above.

Figure 3:
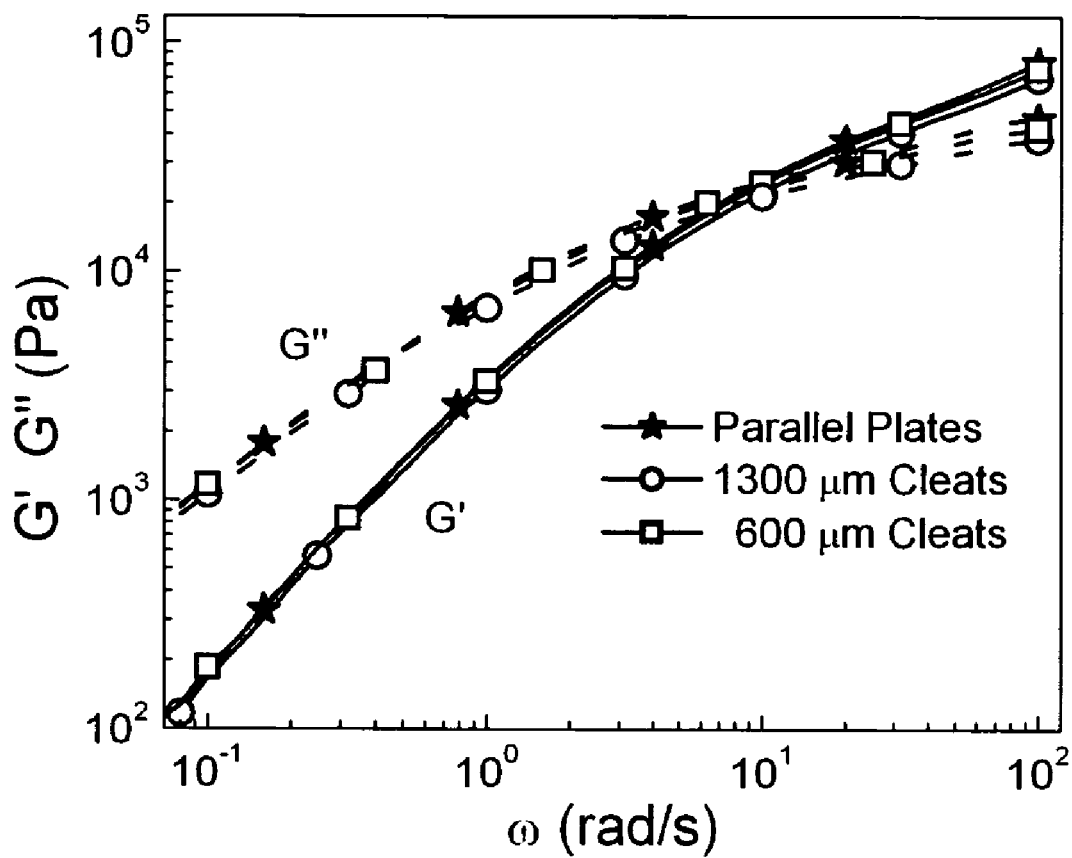
FIG. 3 is a graph of gap corrected shear moduli of PDMS putty verses rotational speed as measured with the cleat geometry of the invention. The values of gap corrected shear moduli are within 1% of values obtained using a titanium parallel plate over three decades of rotational frequency and modulus ($\gamma$=0.2%, $gap_{meas}$=2 mm).

Consider the results with PDMS putty. The uncorrected storage and loss moduli of PDMS putty ($\eta_o>10^4$ Pa·s) measured with the two cleated tools 10 were consistently lower than those measured using the smooth parallel plates; however, the 157 μm correction factor brings the cleat measurements within 1% of the parallel plate results as shown in the graph of FIG. 3. G' and G" measurements were accurate over the three decades of frequency examined, and the gap dependence matched that of the Newtonian oils. Thus, $\delta$ appears to be independent of material properties for a wide range of soft materials and fluids, including a complex fluid, as anticipated from the porous medium analogy.

Figure 4A:
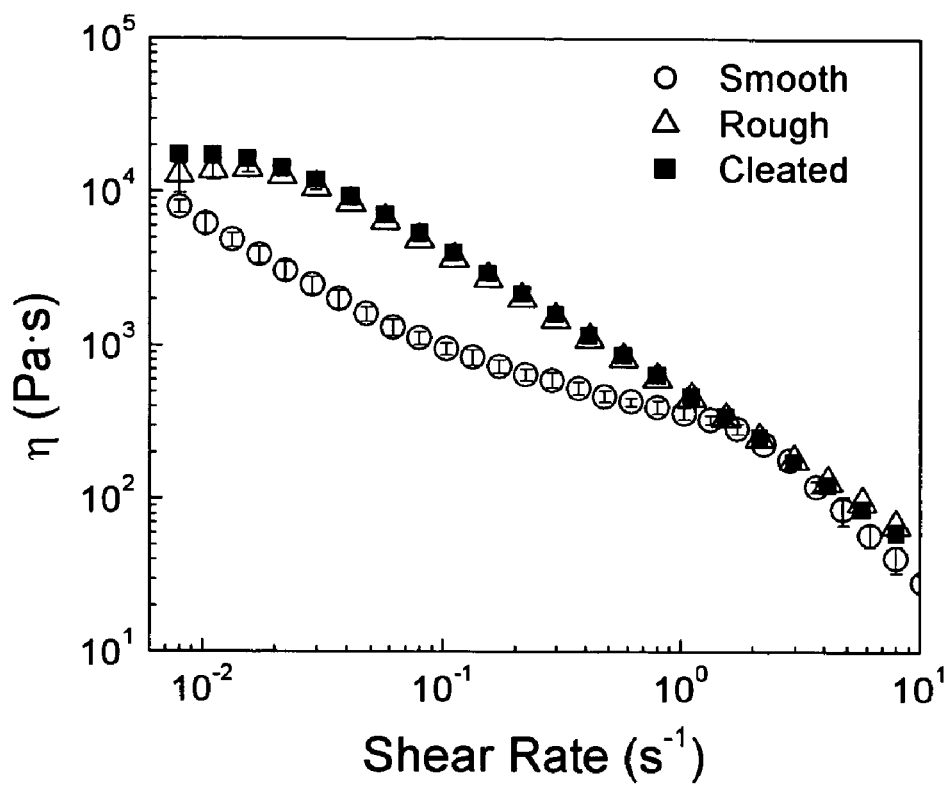
FIG. 4a is a graph of the corrected viscosity of peanut butter and FIG. 4b is a graph of the corrected viscosity of mayonnaise verses shear rate measured with cleated and rough plates. Smooth plates show slip at low shear rates. ($gap_{meas}$=2 mm)
Figure 4B:
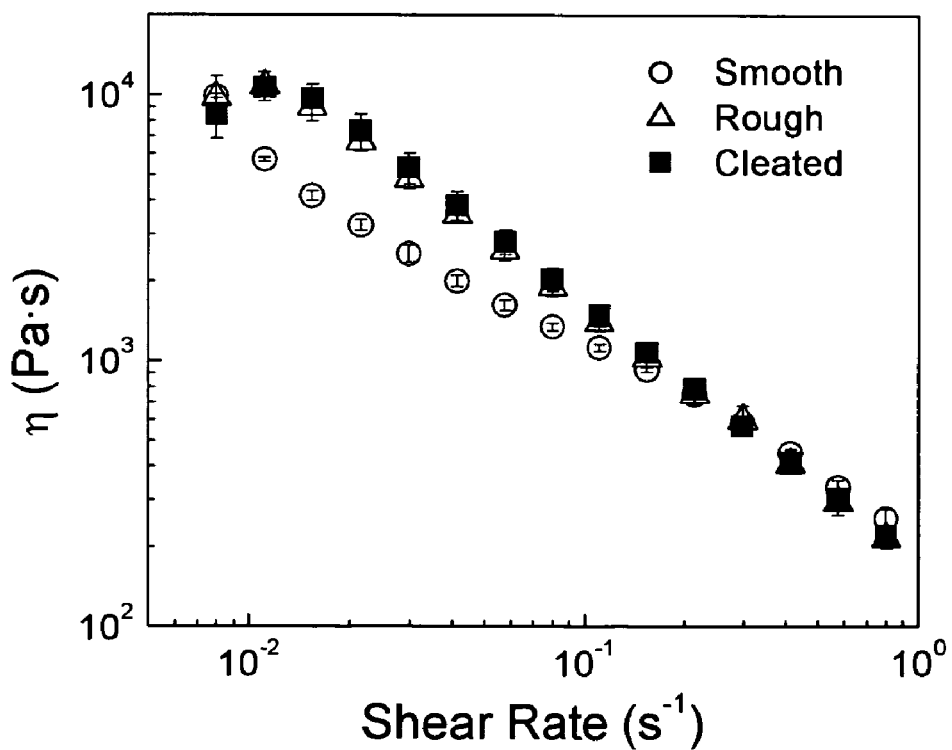

Consider now the result for peanut butter and mayonnaise. The viscosity of peanut butter and mayonnaise were measured using smooth, rough, and cleated tools 10 at $gap_{meas}=2$ mm as shown in the graphs of FIGS. 4a and 4b. Prior art shows that roughened plates are adequate to suppress slip for both of these complex fluids. Peanut butter, a typical suspension, and mayonnaise, an oil-in-water emulsion, both exhibit slip at low shear rates on smooth plates, giving apparent values of η much less than values measured with rough plates. The measured viscosity of both samples was essentially the same with cleated or roughened plates. Apparently the characteristic feature sizes of both tools were larger than the thin depletion layers that cause slip.

Figure 5:
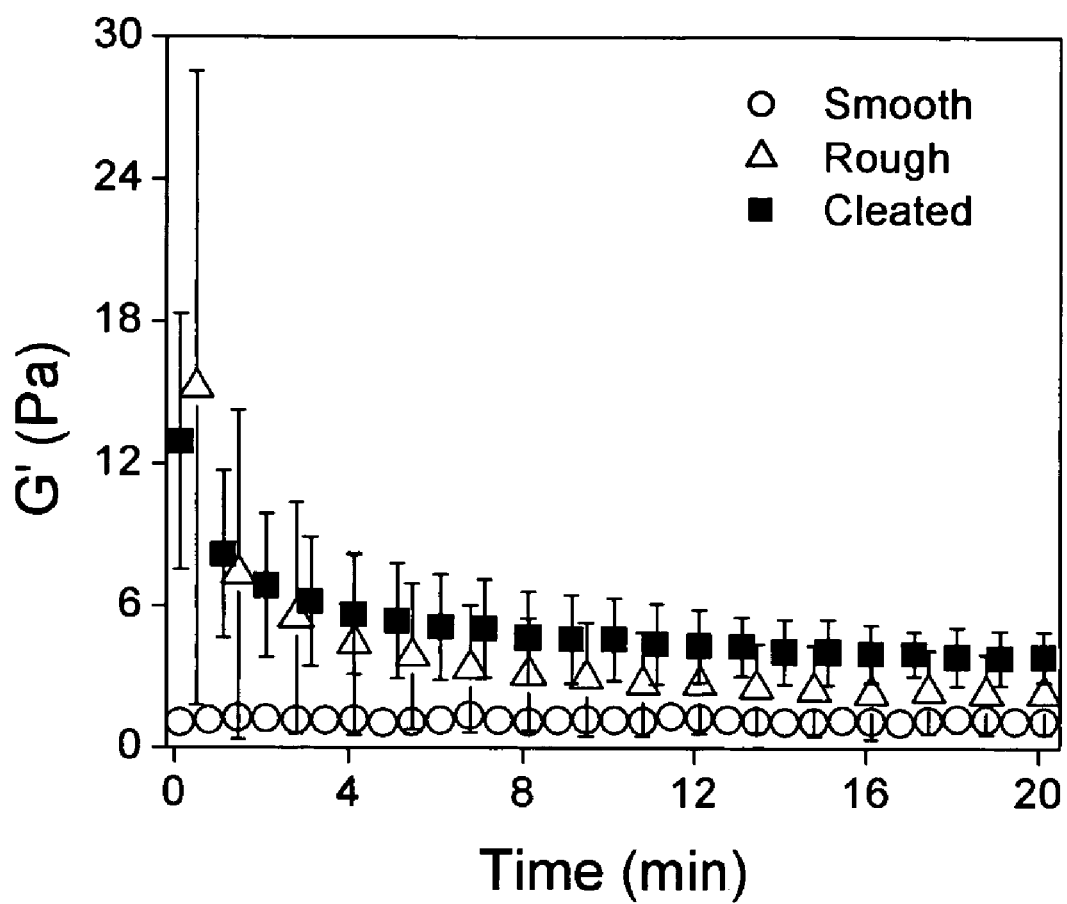
FIG. 5 is a graph of the corrected shear modulus of freshly-enucleated vitreous humor verses time as measured with the cleat geometry, rough plates and smooth plates. The results are far more consistent than for rough plates and clearly more accurate than smooth plates ($\gamma$=3%, $\omega$=10 rad/s).

Consider the results for vitreous humor. Results obtained from the vitreous humor of the eye demonstrate the utility of the cleat geometry for more difficult samples. Previous efforts to measure the mechanical properties of the eye have yielded unsatisfactory and sometimes conflicting results. The shear moduli of this delicate tissue were also impossible to measure using previously published geometries in our laboratory as shown in the graph of FIG. 5. Smooth plates slipped drastically and roughened plates were insufficient because slip was not consistently prevented as seen in the extremely large standard deviation. While some vitreous samples appeared to be measured accurately on the rough fixtures, other loadings appeared to fail (slip) from the first data point, yielding results similar to those obtained with the smooth tools. The normal force required to obtain measurements with roughened tools artificially raised the apparent modulus in the initial data points. Over the course of the experiment the apparent modulus fell with the normal force as fluid was squeezed out of the tissue. In conjunction with fluid loss, a thick lubricating layer formed within five minutes, making it impossible to eliminate slip using roughened plates. In previous efforts to measure the modulus of the vitreous, using porous plates failed for the same reasons as roughened plates and the vane geometry was unsuitable because it destroyed the gel network and sample volume is limited to the size of a single eye.

Using the cleat geometry, these obstacles appear to have been overcome and consistent shear moduli were measured. The modulus values measured with the cleat geometry are slightly greater than those obtained with roughened tools, but the most obvious improvement is the reduction in standard deviation as shown in FIG. 5. Comparing results obtained using the cleat geometry with literature values obtained using other methods suggests that the shear moduli of the vitreous are significantly higher than reported in the works mentioned above. The cleat geometry has also allowed us to quantify time-dependent modulus changes that were previously reported only as qualitative observations.

The illustrated embodiment provides as examples two families of cleated fixtures 10: (1) fixtures 10 to which an array of protrusions 14 are affixed and (2) fixtures 10 into which an array of protrusions 14 are machined, molded or otherwise integrally formed. Arrays of protrusions 14 on a substrate are widely available (for example, Velcro®) and may be cut to desired dimensions and attached to the surface of conventional parallel plates using an adhesive. Typical dimensions of the protrusions 14 are approximately 0.050" long, approximately 0.025" apart, made of wire or plastic rods approximately 0.01" in diameter. Periodic arrays of protrusions 14 may also be created by machining, plasma etching, chemical etching or other equivalent processes. Alternatively protrusions 14 may be separable manufactured and glued onto fixture 10 or held in a matrix layer through which protrusions 14 penetrate and from which protrusions 14 extend, and which matrix layer is in turn affixed to fixture 10. Fixtures 10 having disc radii ranging from 8 mm to 25 mm in diameter have been made. Regular arrays of rectangular protrusions 14 have been machined into metal discs 16. The length of the protrusions 14 was chosen in the range of approximately 0.025" to 0.050". Our smallest dimensions achieved by plasma etching were 50 μm long square posts with edges of length 25 μm and a center to center separation of 50 μm. The width of the protrusions 14 was chosen to be approximately 0.015". The distance between protrusions 14 was chosen to be approximately 0.035". Cleated fixtures 10 have been successfully used in the ARES-RFS fluids rheometer, the AR1000 and the AR2000 rheometers manufactured by TA Instruments, Inc. of New Castle, Del., and in the RFS-II fluids rheometer and ARES v.1.1 rheometer form Rheometric Scientific Inc. of Piscataway, N.J.

We have now built more than six versions of the cleat geometry although many more could be devised. A first embodiment of cleat geometry was fabricated by gluing conventional Velcro® to a parallel plate test geometry. Even this initial, proof-of-concept device proved useful.

A second embodiment of cleat geometry was made in an aluminum disc 16 which was 25 mm in diameter, and which had evenly spaced rows of rectangular protrusions 14. The distal faces 20 were square, approximately 0.015"×0.015", and protruded approximately 0.050" from the parallel face 22 of disc 16. The distance between protrusions 14 within a row or column was approximately 0.035". The back of the disc 16 was fixed to a conventional parallel plate rheometry fixture. This tool geometry was used extensively on the RFS-II fluids rheometer and ARES v.1.1 rheometer from Rheometric Scientific, Inc.

Next, a third embodiment was made with the same dimensions and materials as the second embodiment except that the cleat height was reduced to approximately 0.025". Two more similar embodiments were made with different diameters, namely 8 mm and 15 mm. On both of these fixtures 10 the protrusions 14 were approximately 0.015"×0.015" in width and length and approximately 0.025" in height. The 8 mm tool was affixed to an 8 mm parallel plate geometry and used on an AR1000-N from TA Instruments, Inc.

A sixth family of embodiments was produced lithographically by plasma etching silicon wafers with a number of cleat patterns and at two different heights. A detailed list of the cleat patterns produced, which included hexagonally shaped cleats in addition to square cleats, is as follows. Two wafers were produced, and multiple cleat geometry configurations were etched into each wafer. Wafer 1 was etched 50 μm deep with the tools listed below and wafer 2 was etched 200 μm deep with the same pattern. This left cleats with the following dimensions but differing cleat lengths (50 μm and 200 μm, respectively). The geometric description of tools listed below uses the following abbreviations: Tool number-cleat array pattern (Sq=square, Hex=hexagonal), cleat edge length (25-400 microns per edge of the square), and center-to-center distance between cleats (50-1300 mm)

25 mm Diameter Tools
Sq: 25_50
Sq: 25_500
Sq: 75_150
Sq: 400_1300

8 mm dia
Hex: 25_50
Hex: 25_50
Hex: 25_500
Hex: 25_500
Hex: 75_100
Hex: 75_150
Hex: 75_750

There are a number of variations on the cleat geometry that may be useful which are contemplated as being expressly within the scope and spirit of the invention. First, any number of uniform or non-uniform variations could be made in any one or all of the dimensions, e.g. length, width, and height, and in the shape, e.g. rectangular, circular, polygonal, oblong, hollow, etc.) of the cleat shaft 24 and/or face 20. Protrusions 14 need not all have the same longitudinal length or height, but may be provided a plurality of longitudinal lengths or heights. The exterior walls of shaft 24 also need not be parallel but they could taper toward the top or bottom of protrusion 14 and the faces 20 could have various shapes, e.g. flat, rounded, pointed, etc. The material from which fixture 10 is made could vary as could the density of protrusions 14 and the placement pattern, e.g. evenly spaced, random spacing, geometric patterns, etc. Also, protrusions 14 could be placed on the surfaces of other test geometries than parallel plates, including but not limited to sliding plate, cone-and-plate, Couette, double-Couette, and cup-and-bob geometries. For specimens 12 that undergo slip on only one of their surfaces, a cleated fixture 10 having only one disc 16 provided with protrusions 14 may be used on the problematic surface of sample 12. In many cases slip occurs at both surfaces of sample 12 and protrusions 14 on both discs 16 are then necessary.

Cleat geometry is unique in the way in which it overcomes wall slip, and the systems in which it can be used. Cleat geometry can be used to overcome wall slip in nearly every complex fluid and do so without application of normal force and without destroying native structure. In summary, some of the advantageous features of the illustrated embodiment are:
1. The cleat geometry creates a well-defined "secondary sample boundary" which is away from the tool face 22 and located within the bulk of the material of sample 12 rather than simply modifying the texture of the tool face surface 20.
2. The fixture 10 incorporates part of the sample 12 into the test geometry by trapping it between protrusions 14 and incorporating it into the secondary boundary.
3. Fixture 10 allows accurate rheological measurements even in the presence of a depletion layer.
4. The fixture 10 utilizes a contiguous sample-to-sample interface as the boundary condition and can do so in well-characterized geometries with known flow patterns that are independent of the mechanical properties of the sample.
5. The well-established equations and mathematics of traditional rheometric geometries apply to fixture 10.

The experimental results for Newtonian oils support our hypothesis that the cleats or protrusions 14 create an effective no-slip boundary that is close to the plane of the cleat tips 20. Furthermore, the observation that the ratio of the apparent viscosity observed using cleated tools, $\eta_{meas}$, to actual viscosity, $\eta_{true}$, is independent of the viscosity of the fluid accords with a model that treats the array of cleats as a porous medium. The attenuation distance $\delta=157$ μm inferred from the ratio of $\eta_{meas}/\eta_{true}$ is similar to $5 \cdot k^{1/2}$ determined independently. The experimental observation that the correction factor determined for a series of Newtonian fluids also applies for a viscoelastic fluid (an entangled polymer melt, shown in FIG. 3) over a frequency range that spans from near terminal behavior (G">G') to elastic behavior (G'>G") suggests that the attenuation depth continues to be governed by the geometry of the cleat array even for some non-Newtonian fluids.

The gap dependence of $\eta_{meas}$ is reminiscent of slip phenomena, however the fluid independence of the value, combined with the improbability of slip with the samples chosen, demonstrate that 6 represents a true sample gap boundary-not a slip length. The cleat geometry creates a secondary boundary at a distance $\delta$ below the cleat tips where the no-slip condition effectively holds. The dependence $\eta_{meas}/\eta_{true}=(1+\delta/gap_{meas})^{-1}$ corresponds to the "apparent gap" effect noted by other practitioners in the art. We have shown that an empirical $\delta$ can be inferred that appears to be accurate for the samples investigated and is consistent with the observed dependence of $\eta_{meas}$ on $gap_{meas}$ down to the smallest gap tested ($gap_{meas} \approx 2\delta$).

Optimization of the cleat parameters (height, width, length, and spacing) involves a trade off between minimizing the attenuation length and minimizing the disruption of the sample. Therefore, one can decrease $\delta$ by reducing k through an increase in the area of the cleated surfaces per unit area of the tool. However, increasing the cleat cross-section or density hinders penetration into samples such as gels, elastomers, and biological tissue. The specific parameters of the cleat array we describe have the advantage that only 11% of the nominal surface area (area relevant to penetration) of the disk 16 is occupied by the cleats themselves. This arrangement of well-spaced "pins" readily penetrates diverse complex fluids and certain soft solids. As stated previously, the permeability k of the cleat arrangement determines 6, which subsequently dictates the minimum value of $L_c$. Based on conventional understanding, the optimal length scale of the surface features will decrease as the modulus range of interest increases. They observed that with increasing polymer concentration, i.e. decreasing size of entangled blobs, the optimal sizes of surface features decreases.

Results from the vitreous humor, a complex hydrogel maintained at 99% water in vivo, demonstrate some advantages of the cleat geometry. Highly-charged hyaluronic acid (HA), which draws water into the vitreous in vivo, seeps out of the vitreous when it is removed from the eye. The HA solution that blooms to the surface is a very efficient lubricant, similar to the synovial fluid that lubricates the joints. This HA solution causes the wall slip observed even on very rough surfaces like sandpaper and porous plates. Note that the successful modeling of cleats as porous media does not imply that porous surfaces work as well as cleats. They do not. The advantage of using cleats over standard porous materials such as fritted disks is that the cleats protrude orthogonally from the tool face and engage the sample.

There is an important, transient decrease in modulus that occurs spontaneously after the vitreous is removed from the eye, captured in measurements using the cleat geometry. It is not possible to characterize this transient behavior using roughened plates due to the need to apply a substantial normal force: the strong effects of compression mask the natural decay. Thus, the cleat geometry is uniquely capable of measuring the time-dependent changes in this sample, which is too slippery and fragile to be measured accurately using previously published methods. Because prior mechanical investigations of the vitreous are unsatisfactory, we have no way to independently verify the accuracy of our modulus values. The sample dictates the gap and is destroyed by compression, therefore, the usual procedure to test for slip (varying sample geometry) cannot be applied. The values we report represent a lower bound: potential sources of error in the cleat geometry (wall slip, insufficient surface contact, or increased flow between the cleats) would reduce the apparent modulus. We observed that, near the tools, heterogeneities in the tissue moved with the tool surface; therefore, we believe that the above errors are small.

The modulus values here pertain to the central vitreous, the bulk of the tissue. Previous work by others suggests that different moduli would characterize the tissue near the anterior pole (stiffer).

Thus, in this disclosure we have demonstrated the accuracy of "cleat" geometry for the rheological characterization of a variety of slip-prone materials. This tool 10 is unique in its ability to quantitatively measure shear modulus and viscosity of slip-prone materials without applying significant normal force, without complex data analysis, and without large sample volumes. Even the vitreous humor, which fails in geometries that have been engineered to address wall slip (rough, serrated, vane, helix) appears to be successfully characterized using the cleat geometry. Wall slip can arise from a wide variety of complex physical phenomena, therefore this geometry will be insufficient in some circumstances. However, validation of cleated tools for a variety of fluids, including gels, foods, personal-care products, and industrial products, and ranging over five decades in viscosity ($10^{-1}$-$10^4$ Pa·s) indicates that they are advantageous in diverse systems that exhibit wall slip.

Many alterations and modifications may be made by those having ordinary skill in the art without departing from the spirit and scope of the invention. For example, the illustrated embodiment has shown two opposing, parallel rotational discs 16. However, the tool system also includes all other configurations now known or later devised. Cleats 14 may be provided on any surface or surfaces according to the invention, such as in a rotating cone and planar plate system, in a rotating cup-couette system, in a rotating toroidal cup-couette system, or in relatively translational or vibratory parallel planar plate system.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method of making a rheological measurement of the bulk of a sample comprising:

disposing the sample to be measured between two opposing surfaces of a fixture;

coupling two opposing surfaces of the sample with a corresponding adjacent one of the two opposing surfaces of the fixture to create a secondary sample boundary within the sample; and measuring a rheological parameter of the sample, where coupling two opposing surfaces of the sample with a corresponding adjacent one of the two opposing surfaces of the fixture comprises penetrating at least one of the opposing surfaces of the sample with a plurality of protrusions disposed on the corresponding surface of the fixture.

where the plurality of protrusions have distal ends and where coupling two opposing surfaces of the sample with a corresponding adjacent one of the two opposing surfaces of the fixture to create a secondary sample boundary within the sample comprises creating the secondary sample boundary on a plane in the sample relative to the plurality of protrusions, where at the secondary sample boundary, slip is absent because the interface between the fixture and sample is effectively a contiguous sample-to-sample junction between the fixture and the bulk of the sample to serve as an effective fixture-to-sample boundary for rheological purposes with respect to bulk measurement of the sample.

2. The method of claim 1 where creating the secondary sample boundary at a distal plane in the sample defined by the distal ends of the plurality of protrusions comprises creating the secondary sample boundary in the sample at the distal ends of the plurality of protrusions effectively in the bulk of the sample for rheological purposes.

3. The method of claim 1 where creating the secondary sample boundary comprises creating the secondary sample boundary in the sample in the proximity of the body shaft length of the plurality of protrusions effectively in the bulk of the sample for rheological purposes.

4. The method of claim 1 where coupling two opposing surfaces of the sample with a corresponding adjacent one of the two opposing surfaces of the fixture to create a secondary sample boundary within the sample comprises trapping a portion of the sample adjacent to a planar surface of the bulk of the sample.

5. The method of claim 4 where trapping a portion of the bulk of the sample adjacent to the planar surface of the bulk of the sample comprises trapping the portion of the bulk of the sample in a plurality of protrusions.

6. The method of claim 5 where trapping the portion of the bulk of the sample in a plurality of protrusions comprises incorporating the secondary sample boundary of the bulk of the sample in the trapped portion.

7. The method of claim 1 where coupling two opposing surfaces of the sample with a corresponding adjacent one of the two opposing surfaces of the fixture to create a secondary sample boundary within the sample comprises penetrating a depletion layer on the bulk of the sample.

8. The method of claim 1 where measuring a bulk rheological parameter of the sample comprises measuring the rheological parameter between a contiguous sample-to-sample interface between the bulk of the sample and the fixture, which interface is created by the secondary sample boundary.

9. A fixture used to measure a rheolopical parameter of a sample having a bulk volume comprising:
two opposing surfaces of the fixture between which surfaces the sample to be measured is disposed: and
coupling means defined on at least one of the two opposing surfaces of the fixture for creating a secondary sample boundary within the sample where the coupling means comprises a plurality of protrusions disposed on the corresponding surface of the fixture for penetrating at least one of the opposing surfaces of the sample, there being at least a portion of the bulk volume of the sample into which no protrusions extend.

10. The fixture of claim 9 where the plurality of protrusions have distal ends and where the secondary sample boundary created by the protrusions is defined on a plane in the bulk volume of the sample defined by the distal ends of the plurality of protrusions.

11. The fixture of claim 10 where the plane of the secondary sample boundary in the sample defined by the distal ends of the plurality of protrusions comprises a plane at the distal ends of the plurality of protrusions.

12. The fixture of claim 10 where the protrusions each have a body shaft length and where the plane in the sample defined by the distal ends of the plurality of protrusions comprises a plane of the secondary sample boundary in the proximity of the body shaft length of the plurality of protrusions.

13. The fixture of claim 9 where the coupling means comprises means for trapping a portion of the sample adjacent to the surface of the sample defining an effective interface between the fixture and the bulk volume of the sample.

14. The fixture of claim 9 where the coupling means comprises means for trapping a portion of the sample in a plurality of protrusions while leaving at least a portion of the bulk volume of the sample free of trapping protrusions.

15. The fixture of claim 9 where the coupling means comprises means for incorporating a portion of the sample into the secondary sample boundary while leaving at least a portion of the bulk volume of the sample outside of the secondary sample boundary.

16. The fixture of claim 9 where coupling means comprises means for penetrating a depletion layer on the sample.

17. The fixture of claim 9 where the coupling means comprises means for providing a contiguous sample-to-sample interface between the fixture and the bulk volume of the sample.

* * * * *